United States Patent [19]
Kakoki et al.

[11] Patent Number: 5,162,377
[45] Date of Patent: Nov. 10, 1992

[54] TRANSPARENT COMPOSITION

[75] Inventors: Hiroyuki Kakoki; Shoji Nishiyama; Michihiro Yamaguchi; Yoshimaru Kumano, all of Yokohama, Japan

[73] Assignee: Shiseido Company, Ltd., Tokyo, Japan

[21] Appl. No.: 366,569

[22] Filed: Jun. 15, 1989

[30] Foreign Application Priority Data

Jun. 20, 1988 [JP] Japan ................. 63-150195

[51] Int. Cl.⁵ ............ A61K 47/00; A61K 31/59; A61K 31/355; A61K 31/12; A61K 31/07
[52] U.S. Cl. ..................... 514/772; 514/167; 514/458; 514/681; 514/725; 514/783; 514/777; 514/785; 514/941; 514/975
[58] Field of Search ............ 514/458, 772, 783, 167, 514/681, 725, 777, 785, 941, 975

[56] References Cited

U.S. PATENT DOCUMENTS 4,174,296  11/1979  Kass ..................... 252/312
4,840,970  6/1989  Ohasi et al. ............ 514/690

FOREIGN PATENT DOCUMENTS 53-56315   5/1978  Japan .
58-162517  9/1983  Japan .
59-10511   1/1984  Japan .
59-104313  6/1984  Japan .

OTHER PUBLICATIONS

Handbook of Pharmaceutical Excipients, pub. by Amer. Pharm. Assn. (1986) p. 165.
Remington's Pharmaceutical Sciences 15th edition (1975) pp. 316–317.
Chemical Abstracts, vol. 111, No. 6, 7 Aug. 1989, p. 367, abstract No. 45035s.

Primary Examiner—Frederick E. Waddell
Assistant Examiner—Raymond J. Henley, III
Attorney, Agent, or Firm—Sprung Horn Kramer & Woods

[57] ABSTRACT

A transparent composition containing a phospholipid, at least one cationic or nonionic surfactant, an oily component, and water.

7 Claims, No Drawings

TRANSPARENT COMPOSITION

BACKGROUND OF THE INVENTION

1. Field of the Invention

The present invention relates to a transparent composition formed from an associated product dispersion of an amphiphilic or amphipatic substance having a high safety factor, such as lecithin, and an external treatment composition containing the same. More specifically, it relates to a novel composition having an excellent transparency, stability with a lapse of time, and safety, and formed from a dispersion of an associated product obtained by mixing an amphiphilic substance having a high safety factor, such as lecithin, and a small amount of a surfactant as the solubilizing aid, and an external treatment composition containing the same.

2. Description of the Related Art

Many effective substances, physiologically active substances, and skin drugs are oily substances, and there is a need to develop a transparent system base by which they can be stably formulated. In the prior art, to obtain a transparent system having an oily component formulated therein, a method is known in which a surfactant or ethanol is formulated at a high concentration, but the formulation of these components at a high concentration sometimes causes irritation to the skin, eyes, and mucosa.

To reduce this irritation, a method is known of using lecithin with a high safety factor, which is derived from a natural product, instead of synthetic surfactants, but lecithin has a weak emulsifying power and solubilizing power, and therefore, a highly transparent system cannot be obtained. Further, the system has a poor stability. Also, to increase the transparency by reducing the particle size, a method is known in which, for example, a high pressure emulsifier is used, but in this method, although the transparency immediately after preparation is increased, the stability is poor and the transparency cannot be maintained, and therefore, this method is not practically useful in most cases.

As mentioned above, since lecithin alone cannot provide a required stability, a method is known in which a certain nonionic surfactant or ethanol is used in combination with the lecithin, but to obtain a completely transparent system, a large amount of the nonionic surfactant or ethanol must be used relative to the amount of lecithin used. Further, to enable another oily component to be co-present, the amounts of the nonionic surfactant and ethanol are further increased, whereby irritation again becomes a problem as in the prior art.

Therefore, although methods of obtaining stable transparent systems in which oily components are formulated are known, none of these methods has proved to be successful in practical application.

SUMMARY OF THE INVENTION

Accordingly, the objects of the present invention are to eliminate the above-mentioned disadvantages of the prior art and to provide a transparent composition having an excellent transparency, stability with a lapse of time, and safety.

Another object of the present invention is to provide an external treatment composition containing the above-mentioned transparent composition.

Other objects and advantages of the present invention will be apparent from the following description.

In accordance with the present invention, there is provided a transparent composition comprising an amphiphilic substance, a surfactant, an oily component, and water.

In accordance with the present invention, there is also provided an external treatment composition comprising the above-mentioned transparent composition.

DESCRIPTION OF THE PREFERRED EMBODIMENTS

According to the present invention, a novel transparent composition can be obtained in which oily components are stably formulated with a small amount of a surfactant, to an extent such that there is no danger of irritation, by uniformly dispersing an amphiphilic substance such as lecithin and a small amount of a surfactant in water, and then subjecting the dispersion to a strong shearing force by, for example, an emulsifier capable of providing a shearing force, such as a homomixer.

Accordingly, a novel transparent composition having an excellent transparency, stability with a lapse of time, and safety is provided, and the external treatment composition can be obtained by subjecting a mixed dispersion of an amphiphilic substance with a high safety factor, such as lecithin, and a small amount of a surfactant as the solubilizing aid, to a shearing force by using, for example, a homomixer conventionally used in the production of, for example, cosmetics.

In the present invention, the amphiphilic substance has the property of containing a hydrophobic group and a hydrophilic group in the same molecule; for example, lecithin, a quaternary ammonium salt type synthetic lipid such as dialkyldimethylammonium chloride, and a mixture of a quaternary ammonium salt with a higher alcohol.

As the lecithin, any phospholipid including natural phospholipids, such as soybean lecithin and egg yolk lecithin, synthetic phospholipids such as synthetic glycerophospholipid ester, and hydrogenated products of natural phospholipids (e.g., preferably those having an iodine value of 10 or less). Since all the natural phospholipids contain unsaturated fatty acids, the use of the hydrogenated phospholipids, in which the unsaturated fatty acids are saturated with hydrogen, is preferable and more effective. Note, although synthetic phospholipids are expensive, they can be used in the present invention.

Typical examples of the phospholipids are lecithin, phosphatidyl ethanolamine, phosphatidic acid, phosphatidylinositol, phosphatidylserine, phosphatidyl chlorine, phosphatidyl glycerol, sphingomyelin, and cardiolipin. Furthermore, the hydrogenated products thereof obtained by a conventional method also can be used. But hydrogenated natural lecithins obtained by hydrogenating soybean lecithin, egg yolk lecithin, corn lecithin, cottonseed lecithin, and rapeseed lecithin are preferably used.

In the present invention, the surfactant may be any of nonionic surfactants and ionic surfactants (cationic, anionic, amphoteric), but from the aspect of safety, the nonionic surfactants generally used in cosmetics are preferable. More particularly, there may be included sugar or sugar alcohol fatty acid esters such as sucrose fatty acid esters, and maltitol fatty esters; sorbitane fatty acid esters, glycerine fatty acid esters, polyglycerine fatty acid esters, propylene glycol fatty acid esters, polyoxyethylene sorbitane fatty acid esters, polyoxyethylene sorbitol fatty acid esters, polyoxyethylene glycerine fatty acid esters, polyethylene glycol fatty acid esters, polyoxyethylene alkyl ethers, polyoxyethylene phytosterol, polyoxyethylene polyoxypropylene alkyl ethers, polyoxyethylene alkyl phenyl ethers, polyoxyethylene cholestanol ether, polyoxyethylene castor oil, polyoxyethylene hardened castor oil, polyoxyethylene beeswax derivatives, polyoxyethylene lanolin derivatives, polyoxyethylene alkylamines, and polyoxyethylene alkylamides.

In the present invention, the oily components to be formulated into the system may be any of liquid oil components, solid oil components, semi-solid oil components, or substances not easily solubilized in water. For example, liquid oils such as avocado oil, Tsubaki (camellia) oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, Oenothera tetraptera oil, perilla oil, soybean oil, peanut oil, teaseed oil, kaya oil, rice bran oil, China wood oil, Japanese tung oil, jojoba oil, germ oil, triglycerine, glycerine triocatanoate, and glycerine triisopalmitate; solid fats such as cacao fat, coconut oil, horse fat, hardened coconut oil, palm oil, tallow, sheep fat, hardened tallow, palmkernel oil, lard, cattle bone fat, woodwax kernel oil, hardened oil, cattle leg oil, woodwax, and hardened castor oil; waxes such as beeswax, candelilla wax, cotton wax, carunauba wax, bayberry wax, insect wax, whale wax, montan wax, bran wax, lanolin, capok wax, lanolin acetate, liquid lanolin, sugar cane wax, isopropyl lanolin fatty acid, hexyl laurate, reduced lanolin, jojoba lanolin, rigid lanolin, shellac wax, POE lanolin alcohol ether, POE lanolin alcohol acetate, polyethylene glycol lanolin fatty acid, and POE hydrogenated lanolin alcohol ether; hydrocarbons such as fluid paraffin, ozocerite, squalene, pristane, paraffin, ceresin, squalane, petrolatum, and microcrystalline wax; synthetic esters such as isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprylate, diisostearyl malate, glycerine di-2-heptylundecanoate, trimethylolpropane tri-2-ethylhexylate, trimethyolpropane triisostearate, pentaerythritol tetra-2-ethylhexylate, glycerine tri-2-ethylhexylate, trimethylolpropane triisostearate, cetyl-2-ethylhexanoate, 2-ethylhexylpalmitate, glycerine trimyristate, tri-2-heptylundecanoic acid glyceride, castor oil fatty acid methyl ester, oleic acid oil, cetostearyl alcohol, acetoglyceride, palmitic acid-2-heptylundecyl, diisopropyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, and triethyl citrate; higher fatty acids such as lauric acid, myristic acid, palmitic acid, stearic acid, behenic (behenyl) acid, oleic acid, 12-hydroxystearic acid, undecylenic acid, tall acid, lanolin fatty acid, isostearic acid, linoleic acid, linolenic acid, and eicosapentaenic acid; straight, branched higher alcohols such as lauryl alcohol, cetyl alcohol, stearyl alcohol, behenyl alcohol, myristyl alcohol, oleyl alcohol, cetostearyl alcohol, monostearyl glycerine ether (batyl alcohol), 2-decyltetradecinol, lanolin alcohol, cholesterol, phytosterol, hexyl dodecanol, isostearyl alcohol, and octyl dodecanol; vitamins such as vitamin A and derivatives, vitamin D and derivatives, vitamin E and derivatives, and vitamin K and derivatives; sterols; natural and synthetic perfumes; and so on. Among the above, those having melting points not higher than normal temperature are classified as liquid oil components, and those having melting points at normal temperature or higher are classified as solid or semisolid oil components.

As the substance not easily solubilized (or slightly soluble) in water, there may be included vitamins such as ubiquinone and vitamine P; anti-microbial agents such as chlorohexidine hydrochloride, trichlorocarbanilide, and Irgussan DP 300; drugs such as dexametazone acetate; UV-ray absorbers such as p-aminobenzoic acid (hereinafter abbreviated as PABA), N,N-dimethyl PABA octyl ester, and preservatives such as paraben.

The amounts formulated of the amphiphilic substance, the surfactant, and the oily component are preferably 0.001 to 100 parts by weight, more preferably 0.01 to 10 parts by weight, most preferably 0.01 to 5 parts by weight, of the surfactant per 1 part by weight of the amphiphilic substance.

The total amount of the amphiphilic substance and the surfactant is preferably 50 parts by weight or less, more preferably 20 parts by weight or less, per one part by weight of the oily component.

Among the above, to obtain a nonalcoholic system transparent composition, an amount of as much as several to several tens of parts by weight of surfactants is generally required per one part by weight of the oily component, and even when a combination of a readily solubilizable oily component and a surfactant is used, a nonalcoholic transparent composition cannot be obtained unless a minimum of two parts by weight or more of the surfactant are used. According to the system of the present invention, a composition having a high transparency can be characteristically obtained even at a level of 10 parts by weight or less, especially 1 part by weight or less, of the surfactant per 1 part by weight of the oily component.

The transparent composition of the present invention can be obtained by treating a mixed dispersion containing the above-mentioned essential components in an emulsifier, such as a homomixer, conventionally used in the production of cosmetics. The transparency, safety, and stability of the transparent composition according to the present invention can be further improved when the mixture is treated in an emulsifier capable of providing a stronger shearing force than a conventional homomixer. Examples of such emulsifiers are the Manthon Gaulin, the French press, the colloid mill, the microfluidizer, and the sonication emulsifying machine. This treatment be performed for either the whole amount of the system, or in some cases a part of the system, followed by dilution with other formulations such as water or polyhydric alcohol.

The "strong shearing force treatment" used herein means the treatment in which an emulsifier capable of providing a stronger or higher shearing force than a mixer (e.g., a homomixer, Disper, a propeller type mixer) conventionally used in the production of cosmetics. Examples of such emulsifiers are a high pressure homogenizer (e.g., Manthon Gaulin, French press, Microfluidizer) preferably operating under a pressure of 500 psi or more, more preferably 2000 psi or more, a colloid mill preferably operating at 1000 rpm or more, more preferably 5000 rpm or more, or an ultrasonication emulsifier.

The shearing treatment according to the present invention performed for either the whole amount of the system, or in some cases, a part of the system, followed by dilution with other formulations such as water or polyhydric alcohol.

In the present invention, when performing a preliminary emulsification before the main pressure emulsification, preferably the following steps are taken when formulating the oily component or not easily solubilized substance. Namely, first a part or all of the amphiphilic substance, the surfactant, and the oily substance are dispersed or dissolved into molecules in an aqueous solvent. Note, at this time, in some cases a small amount of water may be added, and in this case, preferably the treatment is conducted by heating and/or a homomixer. Next, an aqueous phase is gradually added to the obtained aqueous solvent phase, and in this case, during and/or after the gradual addition the system is preferably made homogeneous by a propeller system stirrer or homomixer.

As the aqueous solvent, there are included, for example, ethanol, isopropyl alcohol, ethylene glycol, propylene glycol, 1,3-butylene glycol, dipropylene glycol, glycerine, polyglycerine such as diglycerine, and triglycerine, tetraglycerine; and glucose, maltose, maltitol, sucrose, fructose, xylitol, inositol, pentaerythritol, sorbitol, malttriose, starch decomposed sugar, and starch decomposed sugar reduced alcohol.

As the aqueous phase, there may be included aqueous solutions of one or more of, for example, water soluble active substances as exemplified by vitamins such as the vitamin B group, vitamin C and derivatives, pantothenic acid and derivatives, and biotin; buffers such as sodium glutamate, arginine, aspartic acid, citric acid, tartaric acid, and lactic acid; chelating agents such as EDTA; UV-ray absorbers such as sodium 2-hydroxy-4-methoxybenzophenone-5-sulfate; various dyes, lower alcohols such as ethanol, isopropyl alcohol; polyols such as ethylene glycol, propylene glycol, 1,3-butylene glycol, glycerol.

The transparent composition of the present invention is obtained as described above.

The transparency, as referred to herein, means a transmittance of 80% or higher when measured by an spectrophotometer at 700 nm, with the transmittance of distilled water taken as 100%.

The transparent composition as described above is utilizable in all fields to which it is applicable i.e., the uses thereof are not limited, but in particular it can be optimally utilized for an external treatment composition; for example, for cosmetics, drugs, and quasi-drugs.

EXAMPLES

The present invention will now be further illustrated by, but is by no means limited to, the following Examples, wherein all parts and percentages are expressed on a weight basis unless otherwise noted.

EXAMPLES 1-3 AND COMPARATIVE EXAMPLE 1

Using the components 1 to 5 shown in Table 1, the aqueous compositions were obtained by the following procedures. Namely, the components 1) to 5) were melted by heating, the system was made homogeneous by a homomixer, the component 6 was gradually added, and a pressure emulsification was carried out by a Manthon Gaulin.

TABLE 1

|  |  | Example | | | Comparative Example |
|---|---|---|---|---|---|
|  |  | 1 | 2 | 3 | 1 |
| 1) | Hydrogenated egg yolk lecithin | 1.5 | 1.0 | 0.5 | 2.0 |
| 2) | POI (30) cholestanol ether | 0.5 | 1.0 | 1.5 | 0 |
| 3) | Squalane | 0.1 | 0.1 | 0.1 | 0.1 |
| 3) | Methylparaben | 0.1 | 0.1 | 0.1 | 0.1 |
| 4) | 1,3-Butylene glycol | 10 | 10 | 10 | 10 |
| 5) | Deionized water | 87.8 | 87.8 | 87.8 | 87.8 |

EXAMPLES 4-6 AND COMPARATIVE EXAMPLE 2

Preparations were prepared in the same manner as in Examples 1-3 and the Comparative Example, except that the Manthon Gaulin was replaced by a homomixer.

Table 2 shows the results of evaluations of the safety, transparency, and stability of Examples 1-6 and Comparative Examples 1-2. The Examples of the present invention were found to have a high transparency, and a very good safety and stability.

The test and evaluation methods used in the Examples and Comparative Examples are as follows:

Safety: Examples and Comparative examples were coated on the forearms of 30 testees, and one overnight closed batch test was conducted, and the evaluations were made.

Transparency: The transmittance at 700 nm was measured, and based on a transmittance of distilled water of 100%, the transmittance of the Examples and Comparative Examples were evaluated.

Stability: The stability after one month was visually evaluated.

TABLE 2

| No. | Safety (No. of testees in which abnormality observed.) | Transparency (% transmittance) | Stability |
|---|---|---|---|
| Example 1 | ○ | 95 | No turbidity and no precipitation |
| Example 2 | ○ | 98 | No turbidity and no precipitation |
| Example 3 | ○ | 95 | No turbidity and no precipitation |
| Example 4 | ○ | 81 | Only slight turbidity and no precipitation |
| Example 5 | ○ | 82 | Only slight turbidity and no precipitation |
| Example 6 | ○ | 81 | Only slight turbidity and no precipitation |
| Comparative Example 1 | ○ | 70 | Remarkable precipitation and separation |
| Comparative Example 2 | ○ | 61 | Remarkable precipitation and separation |

EXAMPLES 7 AND 8

The components 1 to 5 shown in Table 3 were heated and dissolved, followed by making the system uniform in a homomixer. Then, the component 6 was gradually added and emulsified under pressure by a Manthon Gaulin. The safety, transparency, and stability were evaluated as mentioned above. The results are shown in Table 3.

TABLE 3

|  | Example 7 | Example 8 |
|---|---|---|
| 1. Hydrogenated egg yolk lecithin | 1.5 parts | 1.0 parts |
| 2. POE (10) phytosterol ether | 0.5 | 1.0 |
| 3. cholesteryl 12-hydroxystearate | 0.5 | 0.5 |
| 4. Methylparaben | 0.1 | 0.1 |
| 5. 1,3-Butylene glycol | 10 | 10 |
| 6. Deionized water | to 100 | to 100 |
| Safety | ○ | ○ |
| Transparency | 96 | 98 |
| Stability | No turbidity and no precipitation | No turbidity and no precipitation |

As is clear from the results shown in Table 3, the resultant compositions have a high transparency and good safety and stability.

EXAMPLE 9

|  | Parts |
|---|---|
| 1) 1,3-Butylene glycol | 10.0 |
| 2) Hydrogenated egg yolk lecithin | 1.8 |
| 3) POE (60) hydrogenated castor oil | 0.2 |
| 4) Squalane | 0.2 |
| 5) Vitamine E acetate | 0.05 |
| 6) Methylparaben | 0.1 |
| 7) Deionized water | 87.62 |
| 8) Ascorbic acid | 0.03 |

First, the components 1 to 6 were heated at 70° C, and then the components 7 and 8 were gradually added thereto while stirring by a homomixer. Then a treatment by a Manthon Gualin was carried out 10 times at 6000 psi, to obtain an aqueous transparent composition having a transmittance of 90% or higher and stable under room temperature for 6 months or longer.

EXAMPLE 10

|  | Parts |
|---|---|
| 1) Glycerol | 10.0 |
| 2) Propylene glycol | 5.0 |
| 3) Dipalmitoyl phosphotidylcholine | 2.0 |
| 4) POE (20) sorbitane monooleate | 2.0 |
| 5) Cetyl isooctanoate | 0.1 |
| 6) Octyl dimethyl PABA | 0.3 |
| 7) Butylparaben | 0.1 |
| 8) Deionized water | 20.0 |
| 9) Deionized water | 60.5 |

First, the components 1 to 7 were heated at 70° C., and then the component 8 was gradually added while stirring by a homomixer. Then, a treatment was conducted by a sonication emulsifying machine until a transparency was observed, followed by an addition of the component 9 under room temperature to obtain an aqueous transparent cosmetic having a transmittance of or higher, and a stable UV-ray absorption effect under room temperature for 6 months or longer.

EXAMPLE 11

|  | Parts |
|---|---|
| 1) Propylene glycol | 15.0 |
| 2) Cetyltrimethylammonium chloride | 1.5 |
| 3) Hydrogenated soybean lecithin | 3.0 |
| 4) Liquid paraffin | 2.0 |
| 5) Deionized water | 20.0 |
| 6) Deionized water | 58.5 |

First, the components 1 to 4 were heated at 70° C., and then the component 5 was added thereto while stirring by a homomixer. Then the Manthon Gaulin treatments were conducted 5 times at 8000 psi, followed by an addition of the component 6 under room temperature, to obtain a transparent hair rinse agent having a transmittance of 90% or higher and stable for 6 months or longer under room temperature.

A hair rinse agent obtained by the same method, except that the component 3 was omitted and 61.5 parts of 6) were added, was found to have a lower transmittance and a lower stability.

EXAMPLE 12

|  | Parts |
|---|---|
| 1) Glycerine | 5.0 |
| 2) Hydrogenated soybean lecithin | 1.0 |
| 3) POE (14)-2-octyl dodecyl ether | 2.0 |
| 4) Dexamethazone acetate | 0.025 |
| 5) Cetyli isooctanoate | 0.5 |
| 6) Deionized water | 91.475 |

First, the components 1 to 5 were heated at 70° C., and then the component 6 was added while stirring by a homomixer. Then, the Manthon Gaulin treatments were conducted 10 times at 5000 psi to obtain a transparent external agent having an anti-inflammatory action, a transmittance of 90% or higher, and stable under room temperature for 6 months or longer.

EXAMPLE 13

|  | Parts |
|---|---|
| 1) 1,3-Butylene glycol | 10.0 |
| 2) Dipalmitoyl phosphatidylcholine | 1.0 |
| 3) POE (10) cholestanol ether | 1.0 |
| 4) 3,4,4'-trichlorocarbanilide | 0.01 |
| 5) Cetyl isooctanoate | 0.2 |
| 6) Methylparaben | 0.1 |
| 7) Deionized water | 20.0 |
| 8) Deionized water | 67.69 |

First, the components 1 to 6 were heated, and then the component 7 was added while stirring by a homomixer. Then, the Manthon Gaulin treatments were conducted 10 times at 7000 psi, followed by an addition of the component 8 under room temperature, to obtain a transparent external agent having an anti-acne effect, a transmittance of 90% or higher, and stable under room temperature for 6 months or longer.

EXAMPLE 14

|  | Parts |
|---|---|
| 1) 1,3-Butyrene glycol | 10.0 |
| 2) Hydrogenated soybean lecithin | 2.0 |
| 3) POE (60) hydrogenated castor oil | 2.0 |
| 4) Olive oil | 1.0 |
| 5) Vitamine A palmitate | 0.05 |
| 6) Methylparaben | 0.1 |
| 7) Deionized water | 84.85 |

First, the components 1 to 6 were heated at 70° C., and then the component 7 was gradually added while stirring. The mixture was treated ten times under a pressure of 20,000 psi by a French press to obtain an aqueous transparent composition having a transmittance of 90% or more. The transparent composition was stable at room temperature for 6 months.

EXAMPLE 15

|  | Parts |
| --- | --- |
| 1) Glycerine | 10.0 |
| 2) 1,3-Butyrene glycol | 10.0 |
| 3) Hydrogenated soybean lecithin | 1.5 |
| 4) POE (60) hydrogenated castor oil | 0.5 |
| 5) Liquid paraffin | 0.5 |
| 6) Vitamine E acetate | 0.05 |
| 7) Methyl p-benzoate | 0.1 |
| 8) Deionized water | 77.35 |

First, the components 1 to 7 were heated at 70° C., and while stirring by a homomixer, the component was gradually added. Thereafter, the mixture was treated five times at 15000 rpm by a colloid mill to obtain an aqueous transparent composition having a transmittance of 90% or more. The transparent composition was stable at room temperature for 6 months.

EXAMPLE 16

|  | Parts |
| --- | --- |
| 1) Glycerine | 10.0 |
| 2) Dipalmytoyl phosphatidylcholine | 0.5 |
| 3) POE (10) cholestanol ether | 1.5 |
| 4) Chlorohexidine hydrochloride | 0.05 |
| 5) Cetyl isooctanate | 0.5 |
| 6) Deionized water | 87.45 |

First, the components 1 to 5 were heated at 70° C., and while stirring by a propeller agitator, the component 6 was gradually added. Thereafter, the mixture was treated at 10,000 rpm for 10 minutes by a homomixer to obtain a transparent external treatment composition having an anti-microbial effect. The resultant composition had a transmittance of 80% or more and was stable at room temperature for more than 6 months.

EXAMPLE 17

|  | Parts |
| --- | --- |
| 1) Glycerine | 5.0 |
| 2) Hydrogenated soybean lecithin | 2.0 |
| 3) POE (16)-2-octyl dodecyl ether | 0.1 |
| 4) Vitamin E acetate | 0.5 |
| 5) Deionized water | 92.4 |

First, the components 1 to 4 were heated at 70° C., and while stirring by a homomixer, the component 5 was gradually added. Thereafter, the mixture was treated ten times under a pressure of 5000 psi to obtain a transparent composition having a transmittance of 90% or more. The aqueous composition was stable at room temperature for more than 6 months.

The transparent composition of the present invention is a novel transparent composition having an excellent transparency, stability with a lapse of time, and safety, and obtained by subjecting a dispersion of an associated product of an amphiphilic substance with a high safety factor, such as lecithin, and a small amount of a surfactant as the solubilizing aid, to preferably a high or strong shearing force. Particularly, even at 10 parts by weight or less, especially 1 part by weight or less of the surfactant based on 1 part by weight of the oily component, the desired oily component can be formulated stably and have a good transparency, and therefore, the irritation which occurs when a large amount of surfactant is added is avoided, and thus the composition has an excellent safety factor.

Also, the associated product has a small average particle size of 0.1 micron or less, and therefore, it can be applied as an injection agent.

Also, since the composition is aqueous, it is not sticky when used, and when lecithin is used as the amphiphilic substance, a humectant effect can be imparted due to the humectant effect of lecithin itself, and by including another oil component having a emollient effect, and therefore, an excellent external agent such as a cosmetic, quasi-drug, or pharmaceutical preparation can be provided.

We claim:

1. A transparent composition comprising an effective amount of (a) a phospholipid, (b) at least one component selected from the group consisting of nonionic surfactants and cationic surfactants, (c) a cosmetically or pharmacologically acceptable oily component and (d) water, up to 10 parts by weight of the surfactant being present per part by weight of the oily component and 0.001 to 100 parts by weight of the phospholipid being present per part by weight of the surfactant, the composition being produced by treating a mixture of said phospholid, surfactant, oily component and water under a strong shearing force.

2. An external treatment composition comprising an effective amount of (a) a phospholipid, (b) at least one component selected from the group consisting of nonionic surfactants and cationic surfactants, (c) a cosmetically or pharmacologically acceptable oily component and (d) water, up to 10 parts by weight of the surfactant being present per part by weight of the oily component and 0.001 to 100 parts by weight of the phospholipid being present per part by weight of the surfactant, the composition being produced by treating a mixture of said phospholipid, surfactant, oily component and water under a strong shearing force.

3. A transparent composition as claimed in claim 6, wherein the surfactant is at least one nonionic surfactant selected from the group consisting of sugar fatty acid esters, sugar alcohol fatty acid esters, sorbitane fatty acid esters, glycerine fatty acid esters, polyglycerine fatty acid esters, propylene glycol fatty acid esters, polyoxyethylene sorbitane fatty acid esters, polyoxyethylene sorbitol fatty acid esters, polyethylene glycol fatty acid esters, polyoxyethylene alkyl ethers, polyoxyethylene phytosterol, polyoxyethylene polyoxypropylene alkyl ethers, polyoxyethylene alkyl phenyl ethers, polyoxyethylene cholestanol ether, polyoxyethylene castor oil, polyoxyethylene hardened castor oil, polyoxyethylene beeswax derivatives, polyoxyethylene lanolin derivatives, polyoxyethylene alkylamines, and polyoxyethylene alkylamides.

4. A transparent composition as claimed in claim 1, wherein the oily component is at least one component selected from the group consisting of liquid oil components, solid oil components and semi-solid oil components.

5. A transparent composition as claimed in claim 1, wherein said strong shearing force is established by operating a high pressure homogenizer under a pressure of at least 500 psi, a colloid mill at least 1000 rpm, or an ultrasonication emulsifier.

6. A transparent composition as claimed in claim 1, wherein the oily component is not easily solubilized in water.

7. A transparent composition as claimed in claim 2, wherein said strong shearing force is established by operating a high pressure homogenizer under a pressure of at least 500 psi, a colloid mill at least 1000 rpm, or an ultrasonication emulsifier.

* * * * *

UNITED STATES PATENT AND TRADEMARK OFFICE
CERTIFICATE OF CORRECTION

PATENT NO. : 5,162,377

DATED : November 10, 1992

INVENTOR(S) : Kakoki et al.

It is certified that error appears in the above-identified patent and that said Letters Patent is hereby corrected as shown below:

```
Col. 10, claim 3    Delete " 6 " and substitute -- 1 --
line 1
```

Signed and Sealed this

Third Day of May, 1994

Attest:

Attesting Officer

BRUCE LEHMAN

Commissioner of Patents and Trademarks